（12） United States Patent
Froehlich et al.

(10) Patent No.: US 10,272,266 B2
(45) Date of Patent: Apr. 30, 2019

(54) RADIATION BEAM POSITIONING

(71) Applicant: Brainlab AG, Munich (DE)

(72) Inventors: Stephan Froehlich, Aschheim (DE);
Kajetan Berlinger, Munich (DE);
Richard Wohlgemuth, Bad Tolz (DE)

(73) Assignee: Brainlab AG, Munich (DE)

( * ) Notice: Subject to any disclaimer, the term of this patent is extended or adjusted under 35 U.S.C. 154(b) by 294 days.

(21) Appl. No.: 15/322,576

(22) PCT Filed: Jul. 3, 2014

(86) PCT No.: PCT/EP2014/064189
§ 371 (c)(1),
(2) Date: Dec. 28, 2016

(87) PCT Pub. No.: WO2016/000777
PCT Pub. Date: Jan. 7, 2016

(65) Prior Publication Data
US 2018/0200535 A1 Jul. 19, 2018

(51) Int. Cl.
*A61B 6/00* (2006.01)
*A61N 5/10* (2006.01)
(Continued)

(52) U.S. Cl.
CPC .......... *A61N 5/1049* (2013.01); *A61B 6/486* (2013.01); *A61B 6/527* (2013.01); *A61B 6/5264* (2013.01);
(Continued)

(58) Field of Classification Search
CPC .. A61N 5/1049; A61N 5/1067; A61N 5/1068;
A61N 2005/105;
(Continued)

(56) References Cited

U.S. PATENT DOCUMENTS 6,144,875 A   11/2000  Schweikard et al.
6,501,981 B1  12/2002  Schweikard et al.
(Continued)

OTHER PUBLICATIONS

Li et al., "A novel analytical approach to the prediction of respiratory diaphragm motion based on external torso volume change", Physics in Medicine and Biology, Institute of Physics, vol. 54, No. 13, Jul. 7, 2009, pp. 4113-4130, Publishing, Bristol, GB.
(Continued)

*Primary Examiner* — Courtney D Thomas
(74) *Attorney, Agent, or Firm* — Tucker Ellis LLP

(57) ABSTRACT

The present invention relates to correlating a position of a radiation beam with a position of a target to be irradiated which is contained in a structure having a repetitive motion comprising a plurality of successive motion cycles. External position data is acquired, which describes a position the structure during different motion cycles and/or time periods. Target data is acquired, which describe a position of the target during the motion cycles and/or time periods. A correlation model is generated, which correlates the external position and the target position. A predicted target position during a motion cycle is determined based on the correlation model and acquire external position data. Primary verification data is determined that describes an difference between actual and predicted target position. When the prediction is accurate, a further prediction and verification of the target position in later motion cycles can be performed.

20 Claims, 3 Drawing Sheets

Figure 1:
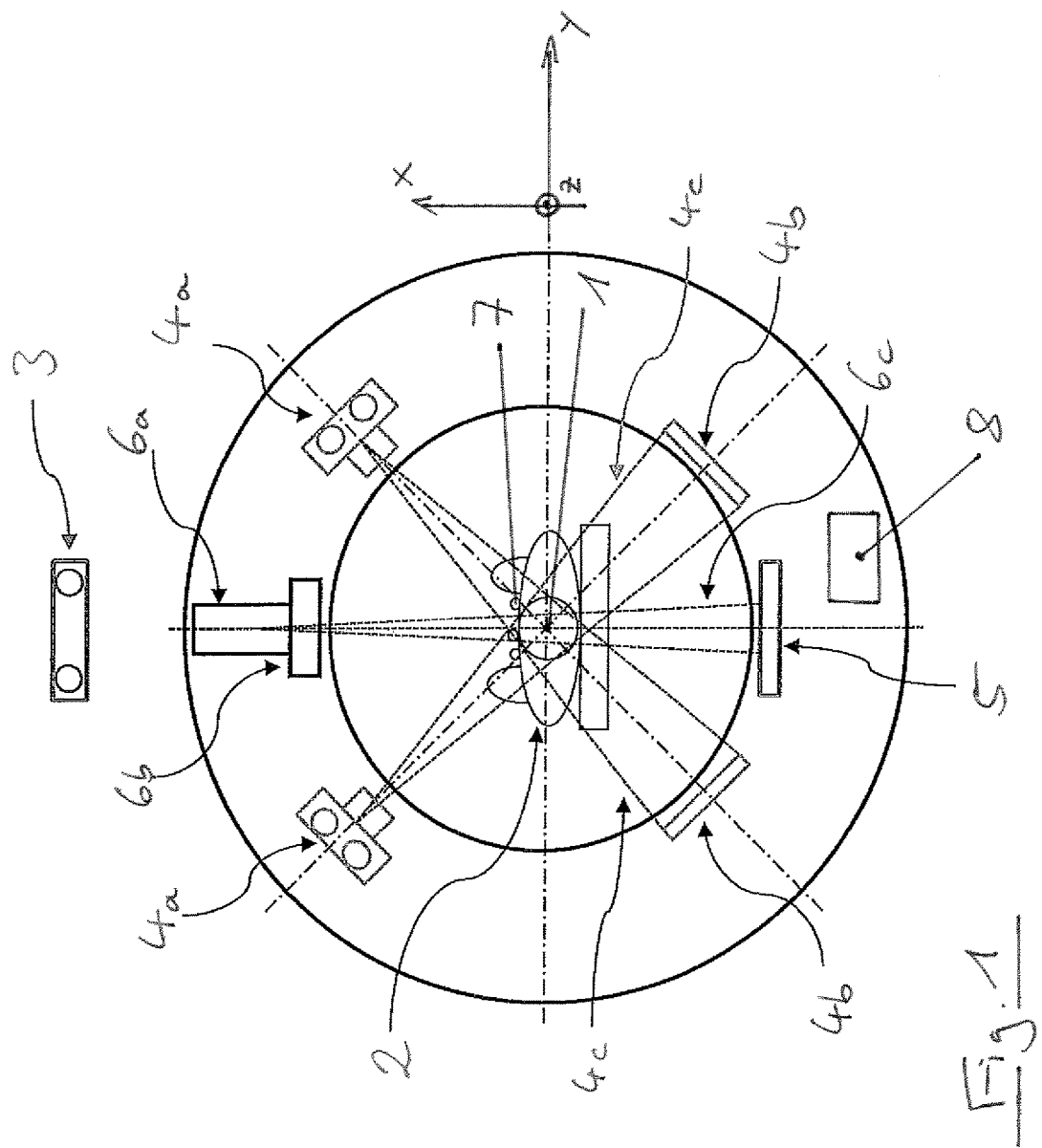

(51) Int. Cl.
*G16H 30/20* (2018.01)
*A61B 90/00* (2016.01)
*A61B 34/20* (2016.01)

(52) U.S. Cl.
CPC .......... *A61B 6/5288* (2013.01); *A61N 5/1067* (2013.01); *A61N 5/1068* (2013.01); *G16H 30/20* (2018.01); *A61B 2034/2055* (2016.02); *A61B 2090/3937* (2016.02); *A61B 2090/3945* (2016.02); *A61B 2090/3966* (2016.02); *A61N 2005/105* (2013.01); *A61N 2005/1051* (2013.01); *A61N 2005/1052* (2013.01); *A61N 2005/1054* (2013.01); *A61N 2005/1058* (2013.01); *A61N 2005/1059* (2013.01); *A61N 2005/1061* (2013.01)

(58) Field of Classification Search
CPC .... A61N 2005/1051; A61N 2005/1052; A61N 2005/1054; A61N 2005/1058; A61N 2005/1059; A61N 2005/1061; G16H 30/20; A61B 6/486; A61B 6/5264; A61B 6/527; A61B 6/5288; A61B 2034/2055; A61B 2090/3937; A61B 2090/3945; A61B 2090/3966
See application file for complete search history.

(56) References Cited

U.S. PATENT DOCUMENTS

| | | | |
|---|---|---|---|
| 7,922,391 B2 | 4/2011 | Essenreiter et al. | |
| 8,391,955 B2 | 3/2013 | Erbel et al. | |
| 8,597,211 B2 | 12/2013 | Berlinger | |
| 2007/0015991 A1* | 1/2007 | Fu | A61B 8/08 600/407 |
| 2009/0110238 A1 | 4/2009 | Li et al. | |
| 2012/0253178 A1 | 10/2012 | Mostafavi | |
| 2012/0316425 A1 | 12/2012 | Raleigh et al. | |

OTHER PUBLICATIONS

International Search Report for PCT/EP2014/064189 dated Sep. 9, 2014, pp. 1-5, European Patent Office, NL.

Written Opinion of the International Searching Authority for PCT/EP2014/064189, pp. 1-7, European Patent Office, Munich, DE.

Ziv R. Yaniv, "Flouroscopic X-ray Image Processing and Registration for Computer-Aided Orthopedic Surgery", Thesis, Institute of Computer Science, The Hebrew University of Jerusalem, Oct. 1, 1998, pp. 1-65, Jerusalem Israel.

Roger Y. Tsal, A Versatile Camera Calibration Technique for High-Accuracy 3D Machine Vision Metrology Using Off-the-Shelf TV Cameras and Lenses, IEEE Journal of Robotics and Automation, vol. RA-3, No. 4, Aug. 1987, pp. 323-344, Yorktown Heights, NY.

* cited by examiner

| Breathing signal | Target Position | Target Position calculated | EPID image |
|---|---|---|---|
| x1, | | x1, y1, z1 | |
| x2 | x2, y2, z2 | x2, y2, z2 | ◉ |
| x3 | | x3, y3, z3 | |
| x4 | | x4, y4, z4 | ◉ |
| x5 | x5, y5, z5 | x5, y5, z5 | ◉ |
| x6 | | x6, y6, z6 | |
| x7 | x7, y7, z7 | x7, y7, z7 | |
| x8 | | x8, y8, z8 | |
| x9 | | x9, y9, z9 | |
| x10 | | x10, y10, z10 | |
| x11 | x11, y11, z11 | x11, y11, z11 | ◉ |
| x12 | | x12, y12, z12 | |
| x13 | x13, y13, z13 | x13, y13, z13 | ◉ |
| x14 | | x14, y14, z14 | |
| x..., | x..., y..., z... | x..., y..., z... | ◉ |

Correlation Model

Fig. 3

RADIATION BEAM POSITIONING

RELATED APPLICATION DATA

This application is a national phase application of International Application No. PCT/EP2014/064189 filed Jul. 3, 2014 and published in the English language.

The invention relates to the general technical field of positioning a radiation beam with respect to a moving target to be irradiated by that beam.

In procedures aiming at irradiating a moving target, it is desirable to know the exact position of the target at any point in time to allow a precise control of the radiation beam, so that in the end, the target is positioned exactly within the beam and the radiation exposure on matter surrounding the target is reduced to the minimum. The most prominent application of such control methods can be found in the medical field of radiation therapy. Despite the fact that the methods and systems described herein may be applied to any conceivable non-medical purpose, the present invention is, for explanatory purposes, described in the context of radiation therapy, without limiting the invention to that kind of application.

In the field of radiation therapy treatment of targets such as tumors in the lung or the liver, which move according to the patient's respiration activity is challenging. To compensate for tumor/target motion, U.S. Pat. Nos. 6,501,981 B1 and 6,144,875 disclose an apparatus and a method incorporating a first imaging device which periodically generates positional data about the internal target and a second imaging device for continuously generating positional data about one or more external markers attached to the patient's body. The methods described therein however still apply a considerable amount of radiation to tissue surrounding the targets to be irradiated.

A problem to be solved by the invention is therefore to provide a method and a system which further reduces the unwanted radiation exposure to matter/tissue surrounding a target to be irradiated.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature. A feature of one embodiment which adds an additional function to another embodiment can in particular be added to said other embodiment.

According to the present invention, a data processing method is provided for correlating the position of a radiation beam with the position of a target to be irradiated and contained in a structure underlying a repetitive motion comprising a plurality of successive motion cycles, wherein the method comprises the following steps which are constituted to be executed by a computer:

a) acquiring first external position data, second external position data and third external position data describing the position of at least one external feature of said structure, for one or more sections of at least one first motion cycle occurring during a first period of time, for one or more sections of at least one second motion cycle occurring during a second period of time, and for one or more sections of at least one third motion cycle occurring during said second period of time, respectively;

b) acquiring first target position data and second target position data describing the position of said target for at least one of said sections of said at least one first motion cycle, and for said sections of said at least one second motion cycle, respectively;

c) determining, based on said first external position data and said first target position data, correlation model data describing a positional correlation of said external position and said target position;

d) determining, based on said correlation model data and said second external position data, second predicted target position data describing a predicted position of said target for one or more sections of said at least one second motion cycle;

e) determining, based on said second target position data and said second predicted target position data, primary verification data describing whether the position of said target for said sections of said at least one second motion cycles is different from said predicted position;

f) acquiring, in case said primary verification data indicates that the position of said target is not different from the predicted position of said target, auxiliary second target position data and auxiliary third target position data describing the position of said target for one or more sections of said at least one second motion cycle, and of said at least one third motion cycle, respectively;

g) determining, based on said first and/or said second external position data, said auxiliary second target position data and said third external position data, third predicted target position data describing a predicted position of said target for said sections of said at least one third motion cycle;

h) determining, based on said auxiliary third target position data and said third predicted target position data, secondary verification data describing whether the position of said target for said sections of said at least one third motion cycle is different from said predicted position.

According to the present invention, a breathing signal has to be generated at first which represents the repetitive motion of a patient's body, that comprises a plurality of motion/respiration cycles. This breathing signal may be obtained by measuring the position of an external surface or feature of the patient. Although it is conceivable that for this purpose, the x- the y- and the z-position of the surface is measured and recorded, measuring and recording the x-component of the surface's spacial position is considered to be sufficient for most purposes. In this context, the x-direction may constitute a spacial direction which is parallel to the axis that runs through both, the target and the source of radiation generating the radiation beam. This spacial position may be obtained with the help of artificial tracking markers that are attached to the patients skin and can be tracked by means of a medical tracking system, for example an optical tracking system comprising an array of cameras sensitive to infrared light and spherical tracking markers having a surface which reflects light so that a spacial position of these markers can be tracked by means of the optical camera array. In the alternative, any other known tracking system comprising artificial tracking markers that are suitable to be attached to the patient may be employed, for example an ultrasound tracking system having ultrasound-sources and microphones, or a tracking system that comprises coils that measure an electromagnetic field generated by one or more field generators.

Moreover, alternative ways of generating a breathing signal may employ means that "directly" measure the position of the patient's skin. For example, a laser scanner measuring the distance from a predetermined point in space to the patient's skin may be employed, as well as a range camera system detecting a structured light surface projected onto the patient's skin. It is even conceivable to employ a system that generates a breathing signal which is not based on the three-dimensional position of an external structure, but rather measures a recurring quantity which is directly related to the patient's respiration, for example, a spirometer measuring the volume of air inspired and expired by the patient's lung.

In the context of the present invention, the "sections" of the motion cycles may be constituted by discrete points of the motion-cycle-curve. Moreover, within the context of the present invention, corresponding sections/points are compared with each other, wherein correspondency means that substantially the same external position data is detected. This means that sections/points of different respiration cycles, which correspond to each other, for example the peak- or bottom points of a plurality of cycles are compared with each other. Such approach may be referred to as a "phase-based" comparison. Additionally or alternatively, corresponding sections/points of one and the same motion cycle or of different motion cycles may be compared with each other, which are indicated by the same external position but take different places within those motion cycles. For example, a section/point lying within the "inhaling"-part of the motion cycle may be compared to a point/section lying within an "exhaling"-part of the same or any other motion cycle. Such approach could be referred to as a "amplitude-based-comparison".

Before a correlation between the breathing signal/the external position data and the position of the target to be irradiated can be built, data as to the three-dimensional position of the target has to be acquired, which corresponds to the obtained external position data. Any suitable imaging device that is capable of acquiring images of the target within the patient's body may be employed for this purpose. For example, an ultrasound imaging device or an x-ray-imaging device comprising two x-ray generators and image receivers and known in general from the above-mentioned documents may be used. To enhance the step of acquiring data as to the spacial target position, distinctively detectable markers may be positioned in or near the target.

As a next step, a correlation model is built, which relates the external position data to the target position data for an arbitrary number of sections or points of at least one motion cycle occurring during a first period of time or "learning phase". With an increasing number of motion cycles being available as a data basis for generating the correlation model at the end of the learning phase, accuracy of the correlation model will also increase.

After the correlation model has been set up, external position data acquired during a second period of time or "irradiation phase" subsequent to the learning phase will serve as a data basis for calculating or "predicting" the target position for future respiration cycles with the help of the correlation model.

Since the actual target position may deviate from the calculated/predicted target position obtained by using the correlation model, the actual target position has to be determined from time to time using the imaging device described above. Such deviation may for example be caused by a coughing or sneezing patient or even a change in depth of respiration, also known as "base-line-drift".

After having obtained the actual target position by means of the imaging device, the accuracy of the calculated target position obtained from the correlation model can be verified.

The target position may be verified not in a predetermined frequency but rather more often at critical points in time, for example when sneezing, coughing or a base-line-drift is detected in the external position data.

According to the present invention, the amount of radiation exposed to the patient by the first imaging device is reduced by employing a further imaging device providing data that can be used for verification purposes, wherein the data is of a different type than the data provided by the first imaging device, and wherein the second imaging device does not necessitate additional radiation to be applied to the patient, that adds to the radiation that is applied to the patient anyway by means of the device generating the treatment beam. For this purpose, an imaging device configured to detect the radiation beam may be employed, for example an EPID-imaging-device. As an alternative, any ultrasound imaging device, PET-imaging device, SPECT-imaging device or an imaging device configured to perform contrast-agent-based imaging may be employed as well.

In other words, positional data of the target obtained by means of the first imaging device is replaced by data obtained by a second imaging device so as to verify the target's position calculated by means of the correlation model obtained beforehand.

With the second imaging device replacing the first imaging device for verification purposes during the second period of time (radiation phase), the present invention provides a solution for considerably reducing the amount of radiation exposed to the patient.

According to a preferred embodiment of the present invention the step of determining the secondary verification data (step h)) is based on an image-matching-method, particularly by performing a gray-scale-matching-method and/or an outline-matching-method, specifically wherein images obtained by said second imaging device are compared with each other.

Since the secondary verification data may be based on a mere comparison of images obtained by the second imaging device, the exact spacial position of the target as shown on these images is not considered. The second verification data is rather based on determining whether the target shown on an image obtained for one motion cycle occurring during the irradiation phase looks equal to the target shown on an image obtained for a preceding motion cycle. Assuming that the target position has changed between the two images, the target will look different on those two images.

A different looking image of the target will therefore indicate a positional change of the target. It is conceivable that a predetermined threshold value for similarity is employed, so that targets not looking exactly the same but look almost the same, for example due to a poorer image quality will not have the effect that a positional change of the target is assumed. Further, as will be explained further below, the described method is executed in connection with an actively controlled treatment beam generating device that is capable of maintaining the direction of irradiation. In case an imaging device sensitive to the irradiation beam is used, the obtained image of the target will, except for negligible scale-effects caused by a motion of the target towards and away from the irradiating device, always looks at least similar, so that in a preferred embodiment, the step of determining said secondary verification data is based on a comparison of a series of images looking almost identical for a plurality of respiration cycles. In case an articulated treatment beam device capable of maintaining the relative position to the target is used together with a multi-leaf-collimator, the images obtained by means of an EPID-imaging device (more specifically images that may be limited by the multi-leaf-collimator substantially to the extent of the projection of the target and therefore constitute subsections of the overall-image received by the EPID-imaging-device, and that may take different positions within the overall-image according to the relative position of the target and a movable treatment-beam-generating device) are expected to look always the same irrespective of the corresponding value for the external position data. Further, it is conceivable that the matching method comprises image-altering-steps such as morphing said images. This may be done to compensate for effects caused by reasons different from a positional change of the target. Instead of directly comparing the images, the degree of similarity may be compared for a plurality of respiration cycles. In such case, the degree of image-similarity may be stored for a plurality of comparisons, so that a subtle deviation of the target's position is detectable by comparing the values stored for the degree of similarity over a period of time.

According to a further preferred embodiment of the present invention the step of determining the primary verification data (step e)) is based on a comparison of positional coordinates of said target, which are particularly obtained by means of determining the position of at least one marker placed in or close to the target.

In contrast to the resolution of the images obtained for determining the secondary verification data, the resolution of the images obtained for determining the primary verification data is usually high. Since the absolute spacial position of the first imaging device is known, the target's position may be calculated directly from the obtained images.

According to a further preferred embodiment of the present invention, the method further comprises the step of controlling, particularly based on the second predicted target position data, an irradiation device configured to generate the radiation beam/treatment beam, particularly by performing a gating and/or tracking procedure.

In other words, the target position as calculated with the help of the correlation model may be used to control the device generating the radiation beam. Assuming that the radiation beam generating device is capable of moving relative to the patient, the position of the radiation beam relative to the target can be maintained by moving the radiation beam generating device in accordance with the moving target. With a positionally fixed radiation beam generating device, a so-called "gating procedure" may be performed, which means that the beam generating device is turned off for the time the target is not within the beam trajectory, and turned on again for the time the target is within the beam trajectory.

In a further preferred embodiment the primary verification data and the secondary verification data is determined with a predetermined frequency, particularly wherein the frequency with which the secondary verification data is determined is higher than the frequency with which the primary verification data is determined.

Obtaining verification data with the help of the second imaging device with a higher frequency than verification data is obtained with the help of the primary imaging device allows to fill up the gaps between the points in time for which the first imaging device has obtained images, with verification data obtained with the help of the second imaging device. By doing so, accuracy of the verification will be increased with a constant dose of radiation.

On the other hand, the primary verification data and the secondary verification data is, at least temporarily during the second period of time, determined in parallel for the same motion cycles, particularly wherein determining the primary verification data during the second period of time is based on data describing the position of the target at one or more sections of at least one second motion cycle and at one or more sections of at least one third motion cycle, respectively.

Even though the secondary verification data may in some cases render the primary verification data superfluous, the primary verification data and the secondary verification data may be obtained in parallel for the same motion cycles occurring during the irradiation phase.

By doing so, the frequency with which the primary verification data is determined for the irradiation phase may be lower than the frequency with which the primary verification data is determined for the learning phase. In such case the dose of radiation is reduced even further without risking the verification accuracy to decrease.

Determining the primary verification data by obtaining images by the first imaging device may even be stopped and the target position verification may be based on the secondary verification data only during an arbitrary period of time during the irradiation phase. For example, if the primary verification data obtained during one or more motion cycles occurring during the irradiation phase indicates that no change in the target position has occurred, the system may switch over to a mode in which the target position is verified with the help of images obtained by means of the second imaging device, for example the EPID-imaging device.

It is preferred to determine the external position data, the target position data and/or the auxiliary target position data for the same points in time, so that this data can be acquired at a predetermined, preferably synchronized frequency. On the other hand, each of the data/images may be provided with some kind of time feature such as a time stamp, so that data acquired or determined for a certain point in time during a motion cycle can be easily assigned to each other.

According to a further preferred embodiment of the present invention, the primary verification data is determined again in case the secondary verification data indicates that the position of the target is different from the calculated/predicted position of the target.

In other words, the primary verification data serves as control data in case the secondary verification data indicates an altered target position. If, for example, an image comparison of EPID-images indicates an altered target position, x-ray-images are made to determine whether the target really has moved into an unexpected position. In case this assumption is verified by the primary verification data, a new correlation model will be built. This new correlation model may be based on data obtained by means of the first and/or the second imaging device during the irradiation phase, or, if necessary, additionally or alternatively on the basis of data obtained during the learning phase.

As a further measure, the irradiation device is stopped, particularly stopped from generating the radiation beam in case the primary verification data and/or the secondary verification data indicates, particularly consecutively indicates that the position of the target is different from the predicted position of the target.

Moreover, the secondary verification data is determined on the basis of target position data obtained for a predetermined number of the latest motion cycles, particularly in case the primary and/or the secondary verification data determined beforehand indicates that the position of the target is not different from the predicted position of the target.

In other words, the images underlying the secondary verification data may be updated during the irradiation phase. In such case, the secondary verification data is always determined on the basis of the "latest" target position data.

A further aspect of the present invention refers to an irradiation apparatus configured to irradiate targets contained within a structure underlying a repetitive motion comprising a plurality of motion cycles, comprising:
a) a tracking system configured to detect at least one external position of the structure, particularly selected from the group consisting of:
  an optical tracking system;
  an ultrasound tracking system;
  an electromagnetic tracking system;
  a range camera system;
  a laser scanner;
  a spirometer;
b) a first imaging device configured to obtain images of the structure containing the target, particularly selected from the group consisting of:
  an ultrasound imaging device;
  an x-ray imaging device;
c) a second imaging device configured to obtain images of the structure containing the target, particularly selected from the group consisting of:
  an imaging device configured to detect the radiation beam;
  an ultrasound imaging device;
  an imaging device configured to perform contrast-agent-based imaging;
  a PET imaging device;
  a SPECT imaging device;
d) a computer configured to process data received from the tracking system, the first imaging device and the second imaging device, particularly by performing the method steps as described further above, and outputting data for further processing, particularly for controlling the beam generating device.

A further aspect of the present invention relates to a program which, when running on a computer or when loaded onto a computer, causes the computer to perform the method steps as described herein and/or a program storage medium on which the program is stored in particular in a non-transitory form and/or a computer, in particular a cloud computer, on which the program is running or into the memory of which the program is loaded and/or a signal wave carrying information which represents the aforementioned program, which comprises code means which are adapted to perform the method steps as described herein.

In particular, the invention as described herein may be employed in connection with the products VERO® and ExacTrac® of BrainLAB®.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which in particular comprises technical, in particular tangible components, in particular mechanical and/or electronic components. Any device mentioned as such in this document is a technical and in particular tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is in particular part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (in particular on the surface of) a characteristic anatomical structure of the body part can also represent said structure. The landmark can represent the anatomical structure as a whole or only a point or part of it. A landmark can also for example lie on the anatomical structure, which is in particular a prominent structure. An example of such an anatomical structure is the posterior aspect of the iliac crest. Another example of a landmark is one defined by the rim of the acetabulum, for instance by the centre of said rim. In another example, a landmark represents the bottom or deepest point of an acetabulum, which is derived from a multitude of detection points. Thus, one landmark can in particular represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur when moved relative to the acetabulum.

The information on the imaging geometry preferably comprises information which allows the analysis image (x-ray image) to be calculated, given a known relative position between the imaging geometry analysis apparatus and the analysis object (anatomical body part) to be analysed by x-ray radiation, if the analysis object which is to be analysed is known, wherein "known" means that the spatial geometry (size and shape) of the analysis object is known. This means in particular that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The location and in particular orientation of the imaging geometry is in particular defined by the position of the x-ray device, in particular by the position of the x-ray source and the x-ray detector and/or in particular by the position of the multiplicity (manifold) of x-ray beams which pass through the analysis object and are detected by the x-ray detector. The imaging geometry in particular describes the position (i.e. the location and in particular the orientation) and the shape (for example, a conical shape exhibiting a specific angle of inclination) of said multiplicity (manifold). The position can in particular be represented by the position of an x-ray beam which passes through the centre of said multiplicity or by the position of a geometric object (such as a truncated cone) which represents the multiplicity (manifold) of x-ray beams. Information concerning the above-mentioned interaction is preferably known in three dimensions, for example from a three-dimensional CT, and describes the interaction in a spatially resolved way for points and/or regions of the analysis object, in particular for all of the points and/or regions of the analysis object. Knowledge of the imaging geometry in particular allows the location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made in particular to the following publications:

1. "An Efficient and Accurate Camera Calibration Technique for 3D Machine Vision", Roger Y. Tsai, Proceedings of the IEEE Conference on Computer Vision and Pattern Recognition. Miami Beach, Fla., 1986, pages 364-374
2. "A Versatile Camera Calibration Technique for High-Accuracy 3D Machine Vision Metrology. Using Off-the-Shelf TV Cameras and Lenses", Roger Y. Tsai, IEEE Journal of Robotics and Automation, Volume RA-3, No. 4, August 1987, pages 323-344.
3. "Fluoroscopic X-ray Image Processing and Registration for Computer-Aided Orthopedic Surgery", Ziv Yaniv
4. EP 08 156 293.6
5. U.S. 61/054,187

The present invention relates to the field of medicine and in particular to the use of beams, in particular radiation beams, to treat parts of a patient's body, which are therefore also referred to as treatment beams. A treatment beam treats body parts which are to be treated and which are referred to in the following as "treatment body parts". These body parts are in particular parts of a patient's body, i.e. anatomical body parts. Ionising radiation is in particular used for the purpose of treatment. In particular, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, in particular the treatment beam, is in particular used in radiation therapy or radiotherapy, in particular in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_v-mat.php and http://www.varian.com/usioncology/treatments/treatment_techniques/rapidarc.

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, in particular in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device or relative to at least a part of the patient's body. The positional arrangement comprises and in particular consists of at least one beam position, in particular a discrete set of beam positions (for example, two or more different beam positions), or a continuous multiplicity (manifold) of beam positions.

In particular, one or more treatment beams adopt(s) the treatment beam position(s) defined by the positional arrangement simultaneously or sequentially during treatment (in particular sequentially if there is only one beam source to emit a treatment beam). If there are several beam sources, it is also possible for at least a subset of the beam positions to be adopted simultaneously by treatment beams during the treatment. In particular, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

The method in accordance with the invention is a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm, Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, in particular handheld, device such as a smart phone or personal digital assistant or digital media player.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In particular, the invention does not involve or in particular comprise or encompass an invasive step which would represent a substantial physical interference with the body requiring professional medical expertise to be carried out and entailing a substantial health risk even when carried out with the required professional care and expertise. In particular, the invention does not comprise a step of positioning a medical implant in order to fasten it to an anatomical structure or a step of fastening the medical implant to the anatomical structure or a step of preparing the anatomical structure for being fastened to the medical implant. More particularly, the invention does not involve or in particular comprise or encompass any surgical or therapeutic activity. The invention is instead directed in particular to positioning the tool relative to the medical implant, which may be outside the patient's body. For this reason alone, no surgical or therapeutic activity and in particular no surgical or therapeutic step is necessitated or implied by carrying out the invention.

In the following, the invention is described with reference to the enclosed figures which represent preferred embodiments of the invention. The scope of the invention is not however limited to the specific features disclosed in the figures.

Figure 2:
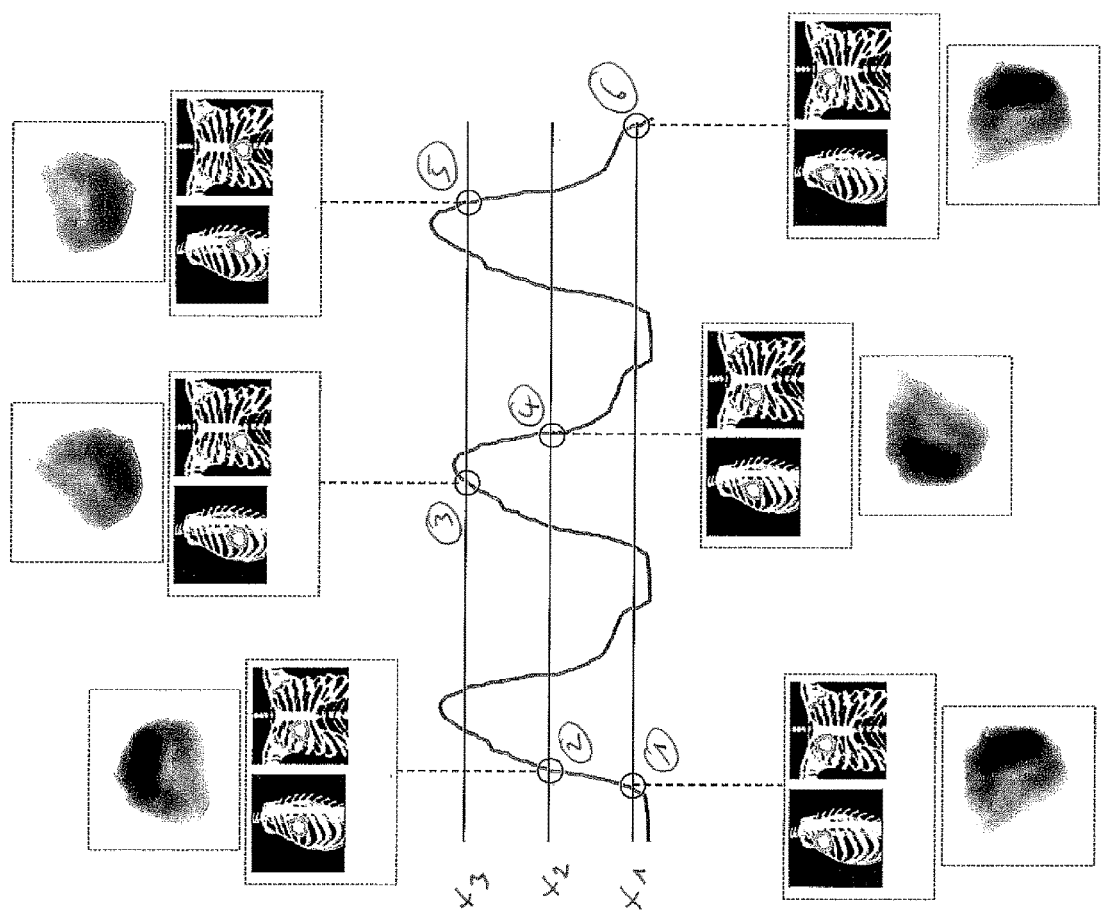

FIG. 1 shows a specific embodiment of an irradiation apparatus according to the present invention;

FIG. 2 schematically shows external position data, target position data and auxiliary target position data determined for a plurality of motion cycles;

FIG. 3 schematically shows data used to determine calculated target position data and verification data.

FIG. 1 shows a specific embodiment of an inventive irradiation apparatus that is configured to irradiate a target 1 contained within a patient 2. Optical tracking markers 7 are adhesively attached to the chest and to the belly of the patient 2, which can be tracked by means of the camera array being part of a tracking system 3. With the tracking markers 7 attached to the patient's skin, a breathing signal is obtained for a plurality of respiration cycles.

The irradiation apparatus further comprises a first imaging device comprising x-ray-sources 4a and x-ray-sensitive receivers 4b, which is able to generate x-ray-images from which corresponding target position data can be acquired for said respiration cycles. The position of the radiation sources 4a and the radiation receivers 4b may be known to the system.

During a so-called learning phase which may last for about 30 to 60 seconds, the position of the target 1 with respect to the tracking markers 7 is recorded for a plurality of respiration cycles, so that in a following irradiation phase (with the radiation beam generating device 6a being turned on), the absolute target position comprising x-, y- and z-components can be calculated with the help of a correlation model obtained at the end of the learning phase.

As the target 1 within the patient 2 may change its position, for example due to a "base-line-drift" of the respiration curve, thereby causing an incorrect calculated target position, the calculated target position has to be verified from time to time during the irradiation phase. This is done by making additional x-ray-images in predetermined intervals which are not necessarily constant but may be shorter for periods of time when a more accurate verification is needed.

In case the actual position of the target conforms to the calculated position obtained from the correlation model, the irradiation device comprising a treatment beam source 6a and a multi leaf collimator 6b may continue with irradiating the target 1.

If, however, the calculated target position deviates from the actual one, a new correlation model has to be built or the irradiation procedure has to be stopped.

In order to reduce the dose of radiation caused by the x-ray-beams during verification, an EPID-device 5 sensitive to the radiation/treatment beam 6c is provided, so that during the irradiation phase, additional data as to the target position is acquired.

The images obtained by means of the EPID-device 5 are however of lower resolution than the x-ray-images obtained by radiation detectors 4b. Further, the exact x-component of the target's position cannot be determined by the EPID-device 5, either.

Therefore, the images obtained by EPID-device 5 are compared with each other by means of an image-matching method so as to determine whether the target's position has changed (EPID-images look different) or still lies within treatment beam 6c (EPID-images look the same or almost the same).

Since image data is obtained by EPID-device 5 at a significantly higher rate than by the x-ray-imaging devices 4a/4b, the inventive method does not only allow to verify the target position with a significantly higher frequence, but does also, at least partially, render the acquisition of x-ray-images superfluous so that in the end, the radiation dose for the patient is reduced.

If, however, EPID-device 5 detects an altered position of the target 1 (EPID-images look different), x-ray-images are made for additional verification purposes. In case the x-ray-imaging device 4a/4b confirms an altered target position (spacial coordinates of the target on the x-ray images are different), a new correlation model will be built to correlate the position of the markers 7 with the position of the target 1 during the irradiation phase again.

The inventive device further comprises a computer 8 which is configured to perform the method steps as described herein, and to output data to a user or to the irradiation device 6a/6b so as to control the position of the treatment beam 6c relative to the target 1.

FIG. 2 schematically shows a process of obtaining target position data, external position data and auxiliary target position data during a plurality of respiration cycles.

Beginning from the left, the respiration curve reaches point/section 1, wherein value $x_1$ is measured as value for the x-component of the target's spacial position. For the same point in time, a two-dimensional EPID-image and x-ray-images providing the three-dimensional position of the target are made.

For each of the remaining points/sections 2 to 6 the same kind of data is acquired.

With the tracking system 3 measuring the same value of x in point 6, it is to be expected that the three-dimensional position of the target within the x-ray images is equal to the position in the x-ray images obtained for point 1. The same applies to the similarity of the EPID-images made for points 2 and 6.

In case any deviation in similarity (EPID-images) or three-dimensional position (x-ray-images) is determined, a change of the target's position has to be expected and appropriate measures have to be undertaken.

FIG. 3 shows how the data obtained may be used to determine whether the predicted target position obtained by means of the correlation model is still valid, and to control the treatment beam source 6a and the multi-leaf-collimator 6b.

For each point in time (indicated with numbers 1 to 6 in FIG. 2), the x-component of the targets position is determined by means of the tracking system 3 and forms the outermost left column. For predetermined points in time, the three-dimensional target position is determined by means of an x-ray-imaging device during a "learning phase", so that a correlation model based on the obtained data can be built. It can be seen that the correlation model may even predict the target's position for x-values of the breathing signal for which the x-ray-imaging device has not provided any target data. This is because the correlation model "creates" a respiration curve (as seen in FIG. 2) which is supported by the positional data acquired by the x-ray-imaging device during the learning phase.

During the subsequent irradiation phase when the treatment beam 6c irradiates target 1, the correlation model may be used to calculate an expected target position from the breathing signal and the external data acquired during the irradiation phase, which forms the third column from the left and is used to control the treatment beam source 6a and the multi-leaf-collimator 6b. A first verification can be obtained by comparing from time to time an for similar values of the breathing signal, the actual target position as determined by means of the x-ray-imaging device with the calculated target position obtained from the correlation model (encircled coordinates in FIG. 3).

Moreover, a second alternative verification is possible by comparing the images obtained from the EPID-imaging device for similar values of the breathing signal.

The invention claimed is:

1. An irradiation apparatus configured to irradiate targets contained within a structure underlying a repetitive motion comprising a plurality of motion cycles, comprising:
   a) a tracking system configured to detect at least one external position of said structure, particularly selected from the group consisting of:
      an optical tracking system;
      an ultrasound tracking system;
      an electromagnetic tracking system;
      a range camera system;
      a laser scanner; and
      a spirometer;
   b) a first imaging device configured to obtain images of said structure containing said target, particularly selected from the group consisting of:
      an ultrasound imaging device; and
      an x-ray imaging device;
   c) a second imaging device configured to obtain images of said structure containing said target, particularly selected from the group consisting of:
      an imaging device configured to detect a radiation beam;
      an ultrasound imaging device;
      an imaging device configured to perform contrast-agent-based imaging;
      a PET imaging device; and
      a SPECT imaging device;
   d) at least one computer having at least one processor configured to process data received from said tracking system, said first imaging device and said second imaging device, by correlating the position of a radiation beam with the position of a target to be irradiated and contained in a structure underlying a repetitive motion comprising a plurality of successive motion cycles, wherein the at least one processor is configured to:
      i) acquire first external position data, second external position data and third external position data describing the position of at least one external feature of said structure, for one or more sections of at least one first motion cycle occurring during a first period of time, for one or more sections of at least one second motion cycle occurring during a second period of time, and for one or more sections of at least one third motion cycle occurring during said second period of time, respectively;
      ii) acquire first target position data and second target position data describing the position of said target for at least one of said sections of said at least one first motion cycle, and for said sections of said at least one second motion cycle, respectively;
      determine, based on said first external position data and said first target position data, correlation model data describing a positional correlation of said external position and said target position;
      iii) determine, based on said correlation model data and said second external position data, second predicted target position data describing a predicted position of said target for one or more sections of said at least one second motion cycle;
      iv) determine, based on said second target position data and said second predicted target position data, primary verification data describing whether the position of said target for said sections of said at least one second motion cycles is different from said predicted position;
      v) acquire, in case said primary verification data indicates that the position of said target is not different from the predicted position of said target, auxiliary second target position data and auxiliary third target position data describing the position of said target for one or more sections of said at least one second motion cycle, and of said at least one third motion cycle, respectively;
      vi) determine, based on said first and/or said second external position data, said auxiliary second target position data and said third external position data, third predicted target position data describing a predicted position of said target for said sections of said at least one third motion cycle; and
      vii) determine, based on said auxiliary third target position data and said third predicted target position data, secondary verification data describing whether the position of said target for said sections of said at least one third motion cycle is different from said predicted position.

2. A computer-implemented data processing method for correlating the position of a radiation beam with the position of a target to be irradiated and contained in a structure underlying a repetitive motion comprising a plurality of successive motion cycles, wherein the program, when running on at least one processor of at least one computer, causes the at least one computer to perform the following method steps:
a) acquiring, at the at least one processor, first external position data, second external position data and third external position data describing the position of at least one external feature of said structure, for one or more sections of at least one first motion cycle occurring during a first period of time, for one or more sections of at least one second motion cycle occurring during a second period of time, and for one or more sections of at least one third motion cycle occurring during said second period of time, respectively;
b) acquiring, at the at least one processor, first target position data and second target position data describing the position of said target for at least one of said sections of said at least one first motion cycle, and for said sections of said at least one second motion cycle, respectively;
c) determining, by the at least one processor and based on said first external position data and said first target position data, correlation model data describing a positional correlation of said external position and said target position;
d) determining, by the at least one processor and based on said correlation model data and said second external position data, second predicted target position data describing a predicted position of said target for one or more sections of said at least one second motion cycle;
e) determining, by the at least one processor and based on said second target position data and said second predicted target position data, primary verification data describing whether the position of said target for said sections of said at least one second motion cycles is different from said predicted position;
f) acquiring, at the at least one processor and in case said primary verification data indicates that the position of said target is not different from the predicted position of said target, auxiliary second target position data and auxiliary third target position data describing the position of said target for one or more sections of said at least one second motion cycle, and of said at least one third motion cycle, respectively;
g) determining, by the at least one processor and based on said first and/or said second external position data, said auxiliary second target position data and said third external position data, third predicted target position data describing a predicted position of said target for said sections of said at least one third motion cycle;
h) determining, by the at least one processor and based on said auxiliary third target position data and said third predicted target position data, secondary verification data describing whether the position of said target for said sections of said at least one third motion cycle is different from said predicted position.

3. The data processing method according to claim 2, wherein said external position data is acquired by means of a tracking system.

4. The data processing method of claim 3, wherein the tracking system has been selected from the group consisting of:
an optical tracking system;
an ultrasound tracking system;
an electromagnetic tracking system;
a range camera system;
a laser scanner;
a spirometer;
said target position data is acquired by means of a first imaging device, particularly selected from the group consisting of:
an ultrasound imaging device;
an x-ray imaging device; and
said auxiliary target position data is acquired by means of a second imaging device, particularly selected from the group consisting of:
an imaging device configured to detect said radiation beam;
an ultrasound imaging device;
an imaging device configured to perform contrast-agent-based imaging;
a PET imaging device;
a SPECT imaging device.

5. The data processing method according to claim 2, wherein the step of determining said secondary verification data (step h) is based on an image-matching method.

6. The method according to claim 5, wherein the image-matching method is at least one of a gray-scale-matching method or an outline-matching-method.

7. The data processing method according to claim 3, wherein the step of determining said primary verification data (step e) is based on a comparison of positional coordinates of said target, which are particularly obtained by means of determining the position of at least one marker placed in or close to said target.

8. The data processing method according to claim 3, further causing the computer to perform the step of controlling, particularly based on said second predicted target position data, an irradiation device configured to generate said radiation beam, particularly by performing a gating and/or tracking procedure.

9. The data processing method according to claim 2, wherein said primary verification data and said secondary verification data is determined with a predetermined frequency.

10. The method according to claim 9, wherein the frequency with which said secondary verification data is determined is higher than the frequency with which said primary verification data is determined.

11. The data processing method according to claim 2, wherein said primary verification data and said secondary verification data is, at least temporarily during said second period of time, determined in parallel for the same motion cycles.

12. The method according to claim 11, wherein determining said primary verification data during said second period of time is based on data describing the position of said target at said one or more sections of said at least one second motion cycle and at one or more sections of said at least one third motion cycle, respectively.

13. The data processing method according to claim 11, wherein the frequency in which said primary verification data is determined for said second period of time is lower than the frequency in which said primary verification data is determined for said first period of time.

14. The data processing method according to claim 2, wherein determining said primary verification data is stopped for said second period of time in case said primary verification data indicates that the position of said target is not different from the predicted position of said target.

15. The data processing method according to claim 2, wherein said external position data, said target position data and/or said auxiliary target position data is assigned to said sections of said motion cycle and to each other by means of a time feature, for example by means of a common time stamp.

16. The data processing method according to claim 2, wherein said primary verification data is determined again in case said secondary verification data indicates that the position of said target is different from the predicted position of said target, in case said primary verification data indicates that the position of said target is different from the predicted position of said target.

17. The data processing method according to claim 13, wherein determining the primary verification data again comprises determining a new correlation model based on target position data that has been already acquired during past motion cycles.

18. The data processing method according to claim 7, wherein said irradiation device is stopped, particularly stopped from generating said radiation beam in case said primary verification data and/or said secondary verification data indicates, particularly consecutively indicates that the position of said target is different from the predicted position of said target.

19. The data processing method according to claim 2, wherein said secondary verification data is determined on the basis of target position data obtained for a predetermined number of the latest motion cycles, particularly in case said primary and/or said secondary verification data determined beforehand indicates that the position of said target is not different from the predicted position of said target.

20. A non-transitory computer-readable program storage medium on which a program is stored which, when executed by at least one processor of at least one computer, causes the at least one processor to execute a computer-implemented data processing method for correlating the position of a radiation beam with the position of a target to be irradiated and contained in a structure underlying a repetitive motion comprising a plurality of successive motion cycles, wherein the program configures the at least one processor to:

a) acquire first external position data, second external position data and third external position data describing the position of at least one external feature of said structure, for one or more sections of at least one first motion cycle occurring during a first period of time, for one or more sections of at least one second motion cycle occurring during a second period of time, and for one or more sections of at least one third motion cycle occurring during said second period of time, respectively;

b) acquire first target position data and second target position data describing the position of said target for at least one of said sections of said at least one first motion cycle, and for said sections of said at least one second motion cycle, respectively;

c) determine, based on said first external position data and said first target position data, correlation model data describing a positional correlation of said external position and said target position;

d) determine, based on said correlation model data and said second external position data, second predicted target position data describing a predicted position of said target for one or more sections of said at least one second motion cycle;

e) determine, based on said second target position data and said second predicted target position data, primary verification data describing whether the position of said target for said sections of said at least one second motion cycles is different from said predicted position;

f) acquire, in case said primary verification data indicates that the position of said target is not different from the predicted position of said target, auxiliary second target position data and auxiliary third target position data describing the position of said target for one or more sections of said at least one second motion cycle, and of said at least one third motion cycle, respectively;

g) determine, by the at least one processor and based on said first and/or said second external position data, said auxiliary second target position data and said third external position data, third predicted target position data describing a predicted position of said target for said sections of said at least one third motion cycle;

h) determining, by the at least one processor and based on said auxiliary third target position data and said third predicted target position data, secondary verification data describing whether the position of said target for said sections of said at least one third motion cycle is different from said predicted position.

* * * * *